(12) United States Patent
Casler

(10) Patent No.: US 6,526,813 B1
(45) Date of Patent: Mar. 4, 2003

(54) METALLURGICAL SAMPLE MAGAZINE

(75) Inventor: Arvid A. Casler, Mundelein, IL (US)

(73) Assignee: Leica Microsystems Inc., Bannockburn, IL (US)

( * ) Notice: Subject to any disclaimer, the term of this patent is extended or adjusted under 35 U.S.C. 154(b) by 156 days.

(21) Appl. No.: 09/668,870

(22) Filed: Sep. 25, 2000

(51) Int. Cl.$^7$ .............................................. G01N 3/48
(52) U.S. Cl. ...................................................... 73/82
(58) Field of Search ....................... 73/81–84; 356/625, 356/626, 628, 629, 635; 348/140, 135

(56) References Cited

U.S. PATENT DOCUMENTS 4,104,901 A * 8/1978 Sidaway ........................ 73/81
5,150,608 A * 9/1992 Mazzoleni et al. ............ 73/81

OTHER PUBLICATIONS

CCSi On–Line Resource Catalog—http://www.ccsi-inc-.com/new/index.htm—Wilson Rockwell MicroHardness Tester Tukon Model 300 Accessories—Universal Clamp and Leveling Device—Part No. 85250—Web Page last Modified Aug. 18, 2000.

* cited by examiner

Primary Examiner—Robert Raevis
(74) Attorney, Agent, or Firm—Simpson & Simpson, PLLC

(57) ABSTRACT

An accessory device for use with a microhardness tester to position a test surface of a sample in a focal plane of the microhardness tester is disclosed. The device comprises a frame having a base that attaches to a z-stage of a microhardness tester, and upstanding front and rear walls connected by a bridge wall spaced vertically from the base. The front and rear walls of the frame each have an inwardly protruding detent rail defining an engagement surface on an underside of the detent rail, wherein the respective engagement surfaces lie in a common plane that corresponds to the focal plane of an objective lens of the microhardness tester. A swivel stage is provided between the front and rear walls for carrying a test sample. The stage is movable automatically or manually to a test position wherein a test surface of the sample abuts with the engagement surfaces in the focal plane and a released position. The frame is preferably elongated in a lateral direction to slidably support a series of samples for successive testing.

23 Claims, 6 Drawing Sheets

METALLURGICAL SAMPLE MAGAZINE

BACKGROUND OF THE INVENTION

1. Field of the Invention

The present invention relates generally to microhardness testers for measuring hardness of a material sample, and more particularly to a device for enabling a series of material samples to be efficiently tested in succession by quickly positioning a test surface of the sample in a focal plane of an objective lens of the microhardness tester.

2. Description of the Related Art

Microhardness testers measure the hardness of a sample material, most commonly a metal, ceramic or composite sample, by deforming a test surface of the sample with a standardized indenter under a known test load to produce an indentation in the test surface, observing a size or depth of the indentation, and correlating the observed size or depth to a predetermined measurement scale. The Vickers, Knoop, Rockwell, and Brinell hardness tests are well-known examples of standardized hardness tests. Microhardness testers are often used in quality control laboratories to check surface treatments such as case hardening of steels, electrodeposited coatings, paint films, and various mechanical and thermal treatments of surface layers. Consequently, samples of various shapes and sizes are encountered, including spherical, cylindrical, and flat samples.

Some microhardness testers, such as the Leica VMHT microhardness tester, are essentially in the form of a microscope that is equipped with indentation means. Accordingly, these instruments include one or more magnifying objective lenses for accurately observing and measuring indentations left on the test surface, and a z-stage for moving the sample relative to an optical axis of a chosen objective lens. The z-stage is adjustable horizontally back-and-forth and side-to-side to locate an indentation within the optical field of view and vertically to position the test surface in the focal plane of the objective lens. The sample is seated in an anvil or secured in a clamp, which in turn may be fastened to the z-stage of the instrument. Anvils are generally designed to cradle the sample in place; for example, V-shaped anvils are common for holding cylindrical samples to test the outer diameter surface of the sample. Various clamps are also available, including a universal clamp and measuring device available from Wilson Instruments of Newport Beach, Calif., that includes an adjustable swivel-mounted stage for supporting a sample and moving the sample relative to a pair of overhead detent members for leveling an upper test surface of the sample by engagement of the test surface with the detent members. Under this design, the test surface can be made level even though a bottom surface of the sample contacting the swiveling stage is not parallel to the test surface.

Heretofore, technicians operating a microhardness tester to test a series of like-sized samples in succession have been slowed by the need to position a test surface of each new sample in a focal plane of the objective lens by adjustment of the instrument z-stage, particularly where slight variations in sample height exist. Where a large number of samples must be tested, as in the case of a production run of manufactured parts, time delays associated with hardness testing can aggregate to significant levels.

BRIEF SUMMARY OF THE INVENTION

Therefore, it is an object of the present invention to provide a device that enables an operator to quickly position a test surface of a sample in a focal plane of a microhardness tester.

It is another object of the present invention to provide a device that enables an operator to more efficiently measure a series of samples by quickly positioning a test surface of each sample in a focal plane of a microhardness tester without the need to readjust a z-stage of the microhardness tester for each measurement.

It is a further object of the present invention to provide a device satisfying the above objects that is easy and inexpensive to manufacture, and that is adaptable for use with microhardness testers presently in use.

In accordance with the present invention, a device comprises a frame having a base that attaches to a z-stage of a microhardness tester under a chosen objective lens. The frame also includes upstanding front and rear walls connected by a bridge wall spaced vertically from the base. The front and rear walls of the frame each have an inwardly protruding detent rail defining an engagement surface on an underside of the detent rail, wherein the respective engagement surfaces lie in a common plane. A stage is provided between the front and rear walls for carrying a test sample with its test surface facing the engagement surfaces of the detent rails, with the stage preferably being mounted on a swivel connection.

The device further comprises means for moving the stage between a test position wherein the test surface is flush with the engagement surfaces on the detent rails, and a released position wherein the test surface is out of surface-to-surface engagement with the engagement surfaces. The particular means for moving the stage can take various forms. In a first embodiment, an automatic arrangement is disclosed wherein the stage is connected to a core rod of a solenoid, whereby the stage is moved when the solenoid coils are energized. In a second embodiment, the stage is connected to a guided member threadably mated in a guide sleeve, and an automatic driver such as a linear motor acts on a radial lever on the guide member to rotate the guide member to achieve axially directed displacement. In a third embodiment similar to the second embodiment, the radial lever extends through an opening in the front wall of the frame for manual operation. Other means for moving the stage, including pneumatic pistons, are also contemplated.

The frame itself is preferably elongated in a lateral direction and the stage resides within an opening in the bridge wall when in the released position, whereby the bridge wall supports more than one test sample moving in a lateral direction through the frame. To facilitate movement of samples laterally through the frame, a pair of PTFE slider strips on which the samples can slide are provided on the bridge wall. A pair of spring strips are provided, one along the inside of the front wall and one along the inside of the rear wall, with spring stops arranged to align a sample on the stage and to maintain spacing between the sample on the stage and adjacent test samples within the frame.

In use, the device is attached to the z-stage of the microhardness tester and the z-stage is adjusted to bring the engagement surfaces of the detent rails coplanar with a focal plane of the objective lens. The operator manually slides a stream of samples through the frame, thereby aligning one of the samples on the stage for testing. The stage is moved automatically or manually to bring the test surface of the sample into contact with the engagement surfaces, thereby positioning the test surface in the focal plane. After testing is completed, the stage is returned to its released position so that the next sample can be aligned with the stage and the testing procedure can be repeated.

BRIEF DESCRIPTION OF THE SEVERAL VIEWS OF THE DRAWINGS

The nature and mode of operation of the present invention will now be more fully described in the following detailed description of the preferred embodiment taken with the accompanying drawing figures, in which.

DETAILED DESCRIPTION OF THE PREFERRED EMBODIMENTS

Figure 1:
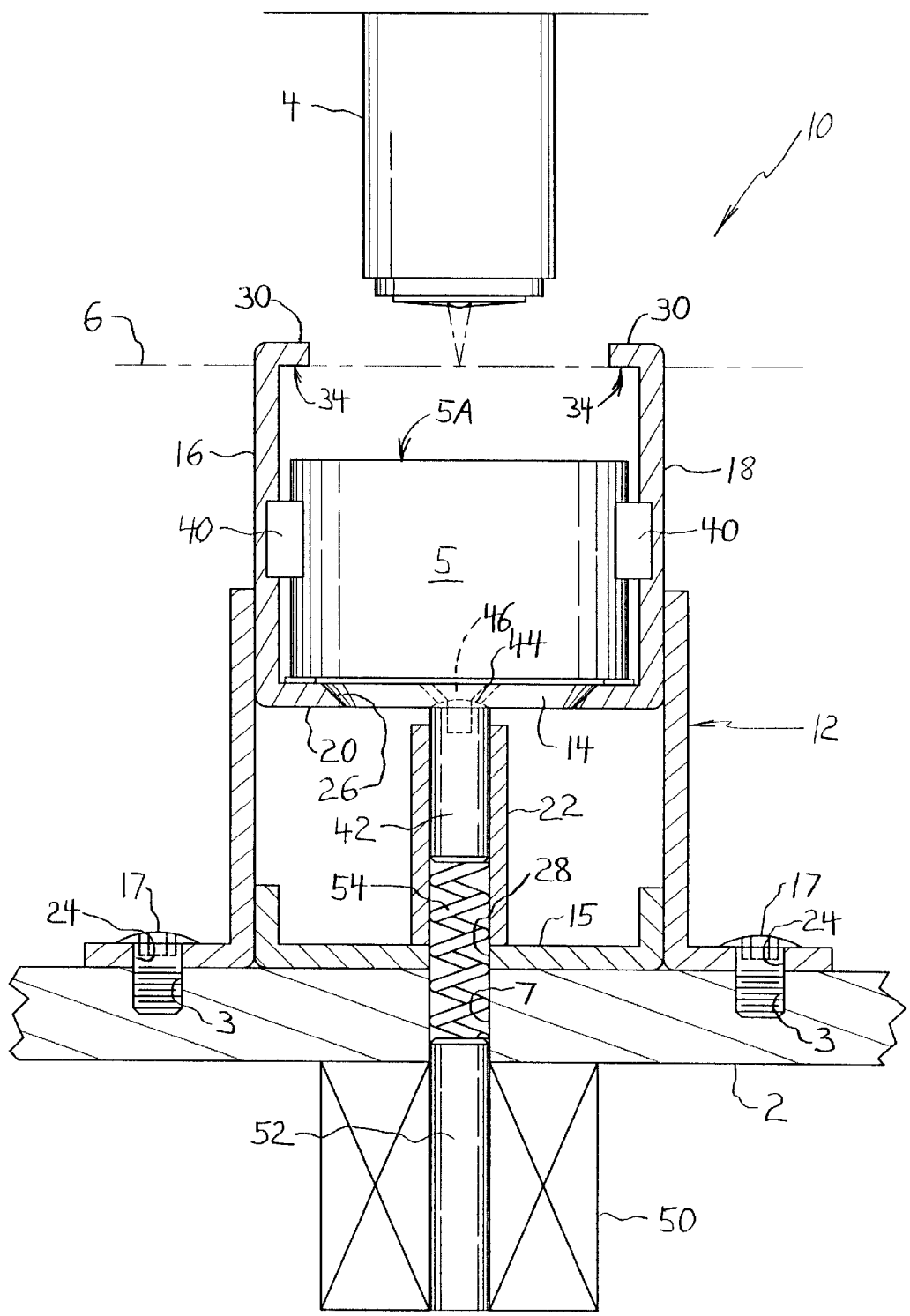
FIG. 1 is a partially sectioned side view of a sample magazine device formed in accordance with a first embodiment of the present invention for use with a microhardness tester, with a stage of the device being shown in a released position.
Figure 2:
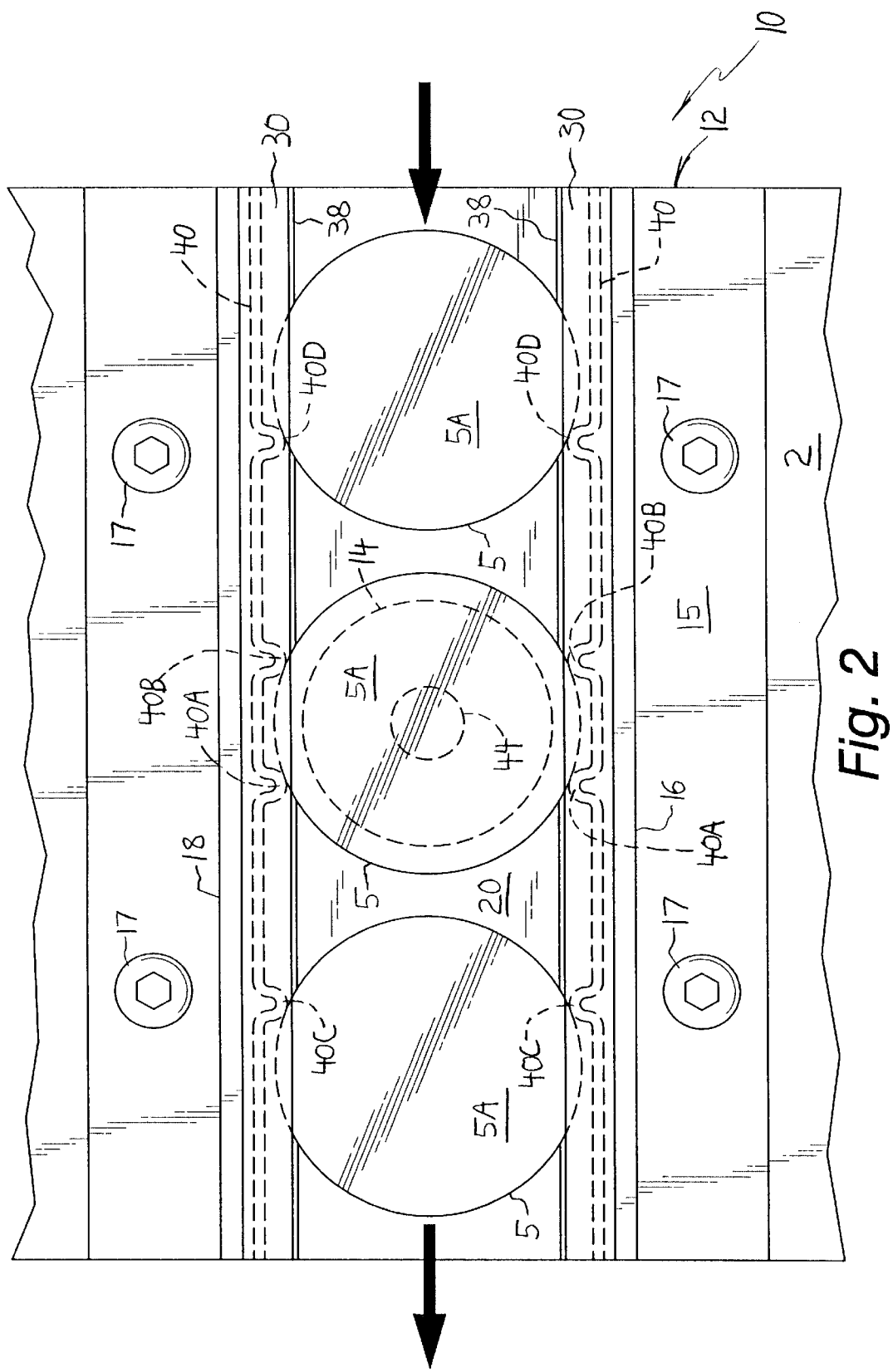
FIG. 2 is a top view of the sample magazine device shown in FIG. 1.

Referring initially to FIGS. 1 and 2 of the drawings, a magazine device formed in accordance with a first embodiment of the present invention is shown and designated generally by the reference numeral 10. Device 10 is an accessory designed for use with a microhardness tester (not shown) having a z-stage 2 and an objective lens 4. More specifically, device 10 is supported on z-stage 2 and serves to releasably position a sample 5 such that a test surface 5A of the sample resides in a focal plane 6 of objective lens 4 for observation of an indentation formed in the test surface by the microhardness tester.

Device 10 generally comprises a frame 12 and a stage 14 vertically moveable relative to the frame for supporting and positioning sample 5. In the preferred embodiments described herein, frame 12 includes a base 15 removably secured to z-stage 2 by a plurality of fasteners 17, a front wall 16 and a rear wall 18 upstanding from base 15 in substantially parallel relation to each other, a bridge wall 20 extending horizontally between front wall 16 and rear wall 18 above base 15, and a guide sleeve 22 extending upwardly from base 15 and terminating a short distance below bridge wall 20. Base 15 is provided with a plurality of through holes 24 alignable with a corresponding plurality of threaded holes 3 for receiving fasteners 17. Bridge wall 20 includes a tapered opening 26 and base 15 includes a passage 28, both opening 26 and passage 28 being axially aligned with guide sleeve 22. Frame 12 can be manufactured by bending, punching, and assembling pieces of carbon steel sheet metal. For example, two pieces can each be bent at right angles to form in the first instance a front portion of base 15 and a lower portion of front wall 16, and in the second instance a rear portion of base 15 and a lower portion of rear wall 18; a third piece can be bent to form a U-shaped channel providing an intermediate portion of base 15 situated between the front and rear walls; and a fourth piece can be bent to form a U-shaped channel with folded-in ends providing bridge wall 20 as well as upper portions of front wall 16 and rear wall 18. Holes 24, tapered opening 26, and passage 28 can be created using a punch press. The constituent pieces of frame 12 can be assembled by resistance or spot welding. While the above description sets forth a preferred economical method of manufacturing frame 12 primarily from sheet metal, it is realized that other methods and materials are of course possible, and that over-the-counter parts may be used in making the frame. Frame 12 is preferably powder coated for corrosion resistance, improved handling, and enhanced cosmetic appearance.

In accordance with the present invention, front wall 16 and rear wall 18 comprise a pair of inwardly protruding front and rear detent rails 30, with each detent rail 30 having a downwardly facing engagement surface 34. The two engagement surfaces 34 are coplanar with each other, and z-stage 2 can be adjusted in the vertical direction to bring engagement surfaces 34 into a coplanar relationship with optical focal plane 6.

FIG. 2 shows device 10, including frame 12, in top view. As will be understood from this view, frame 12 is elongated in a lateral direction such that two additional samples 5 are accommodated on bridge wall 20 on opposite sides of the middle sample aligned with stage 14. As can be inferred from the directional arrows in. FIG. 2, the sample to the left of the middle sample has just been tested, while the sample to the right of the middle sample in FIG. 2 is next in line to be tested. Bridge wall 20 preferably includes a pair of slider strips 38 extending in the lateral direction of travel of the samples 5 through frame 12 near front and rear walls 16 and 18 to facilitate sliding motion of the samples. Thus, slider strips 38 can be any low-friction material, for example polytetrafluoroethylene (PTFE). Front wall 16 and rear wall 18 each include an associated spring strip 40 fixed to an inner facing surface thereof between an associated detent rail 30 above and an associated slider strip 38 below. In the embodiment shown in FIG. 2, each spring strip 40 includes a leading spring stop 40A and a trailing spring stop 40B which cooperate to align each sample 5 relative to stage 14 as the sample travels along slider strips 38. Spring strips 40 are also shown as including an exit spring stop 40C and an entrance spring stop 40D for ensuring some spacing between the sample being tested and other samples traveling through frame 12.

At this point, it is noted that the elongated multi-sample configuration described above is a preferred embodiment, however frame 12 can be made shorter in the lateral direction such that it only holds one sample at a time and aligns the sample on stage 14. If a shortened single-sample configuration is desired, exit spring stop 40C and entrance spring stop 40D are omitted, and slider strips 38 can be omitted.

As shown in FIG. 1, stage 14 is normally located in a released position wherein the stage resides within tapered opening 26 in bridge wall 20 in countersunk fashion such that the sample 5 aligned therewith rests on slider strips 38. Stage 14 is preferably mounted on a guided member 42 by a swivel connection 44 permitting free tilting of the stage within a limited range. Swivel connection 44 is illustrated by engagement of a spherical surface on an underside of stage 14 with a spherical surface on a top end of guided member 42, with a connecting screw 46 having some clearance to allow tilting. It is of course possible to use other types of swivel connections, for example a pure ball-and-socket arrangement.

Figure 3:
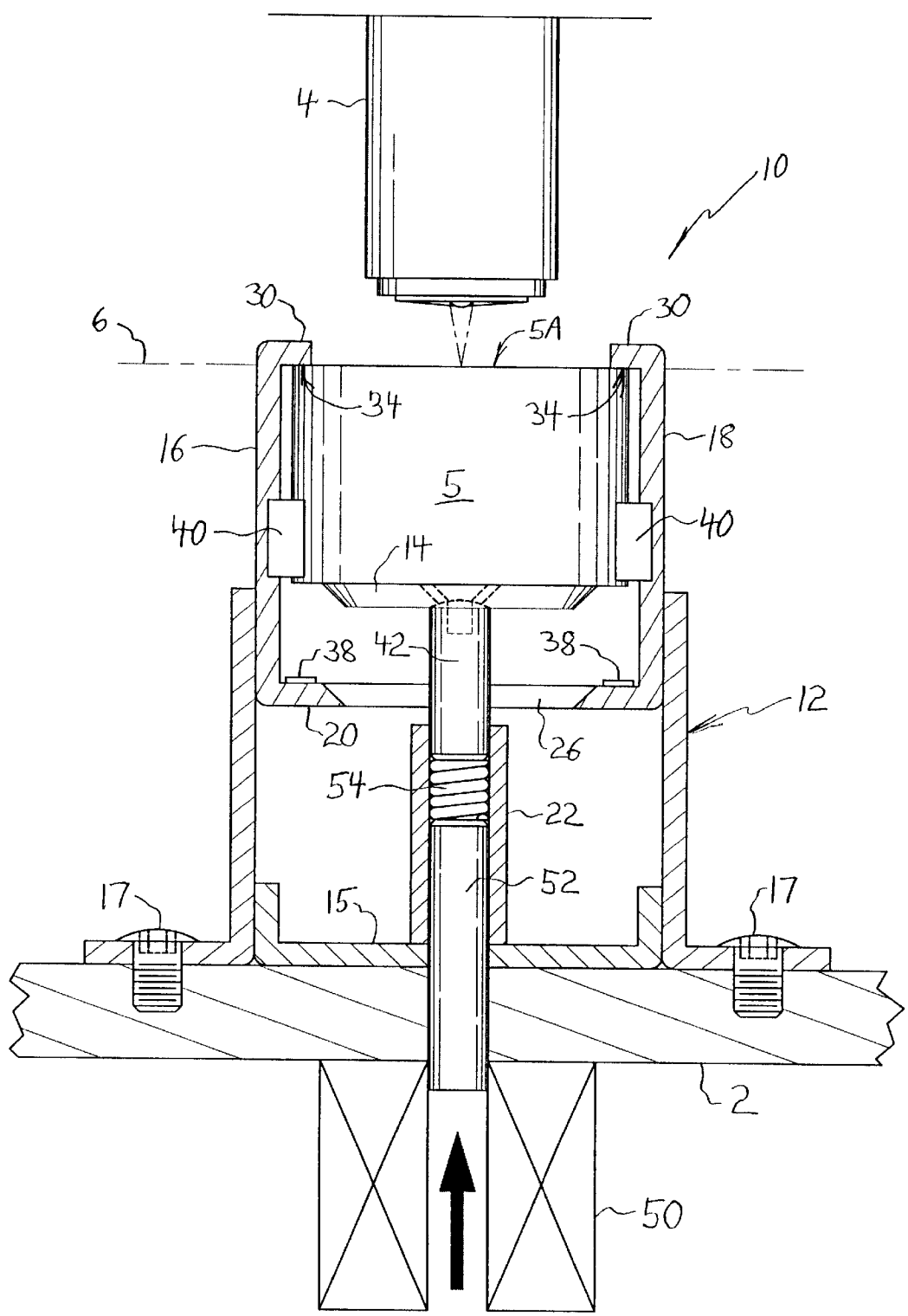
FIG. 3 is a view similar to that of FIG. 1, however showing the stage of the device in a test position.

Means for moving stage 14 according to the first embodiment is now described with additional reference to FIG. 3. Guided member 42 is partially received within guide sleeve 22 for axially directed sliding motion relative to the guide sleeve. A solenoid 50 represented symbolically in the figures is fixed within a cavity beneath z-stage 2 and includes a core rod 52 axially aligned with a hole 7 in z-stage 2, passage 28 in base 15, and guide sleeve 22. Consequently, upon energizing the solenoid coils, core rod 52 travels vertically upward within hole 7, passage 28, and guide sleeve 22 to force guided member 42 and stage 14 upward, thereby causing test surface 5A of sample 5 to reach flush surface-to-surface engagement with engagement surfaces 34. Since the engagement surfaces 34 are coplanar with focal plane 6, they serve to stop test surface 5A in focal plane 6 to define a test position of stage 14. The swivel connection 44 allows flush engagement of test surface 5A with engagement surfaces 34 even when a bottom surface of the sample is not parallel to test surface 5A. A compression spring 54 is situated in series between guided member 42 and core rod 52 to absorb shock and dampen the impact of sample 5 with overhead detent rails 30. A switch and wiring (not shown) connect solenoid 50 to a power source (also not shown) in a known manner to enable selective energizing and de-energizing of the solenoid. As will be appreciated, core rod 52 returns to a reference position under gravity when solenoid 50 is de-energized to allow stage 14 to return to its released position as shown in FIG. 1. In view of the foregoing, samples 5 being tested are quickly positioned vertically to locate test surface 5A in focal plane 6 without further vertical adjustment of z-stage 2.

Figure 4:
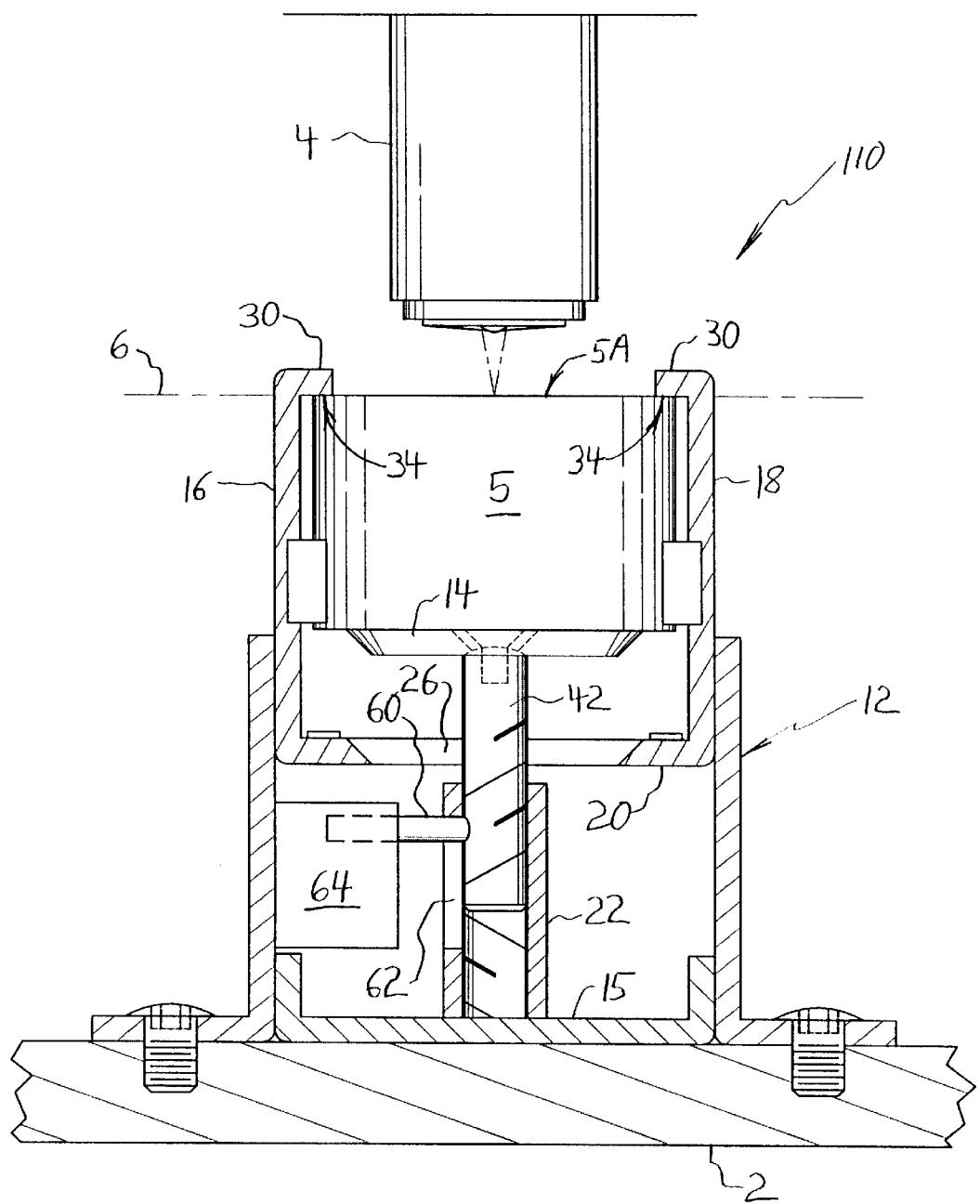
FIG. 4 is a partially sectioned side view of a sample magazine device formed in accordance with a second embodiment of the present invention.

FIG. 4 shows a device 110 formed in accordance with a second embodiment of the present invention that differs from the first embodiment in the means for moving stage 14. In particular, guide sleeve 22 is internally threaded and guided member 42 is a threaded rod mating with the guide sleeve, whereby rotational motion of guided member 42 relative to guide sleeve 22 results in axially directed motion of guided member 42 and stage 14. A lever 60 is arranged to extend radially from guided member 42 through an opening 62 in guide sleeve 22 for operable connection to an automatic driver 64. Automatic driver 64 can be any electromotive device, including a linear motor, rotary motor, linear solenoid, rotary solenoid, or other automatic device arranged to effect bi-directional rotation of guided member 42 by operably engaging lever 60. The threads are preferably coarse in pitch to achieve a relatively large displacement with little rotation. Opening 62 is shaped to allow adequate pivotal motion of lever 60 as well as vertical motion of lever 60 that will accompany the pivotal motion.

Figure 5:
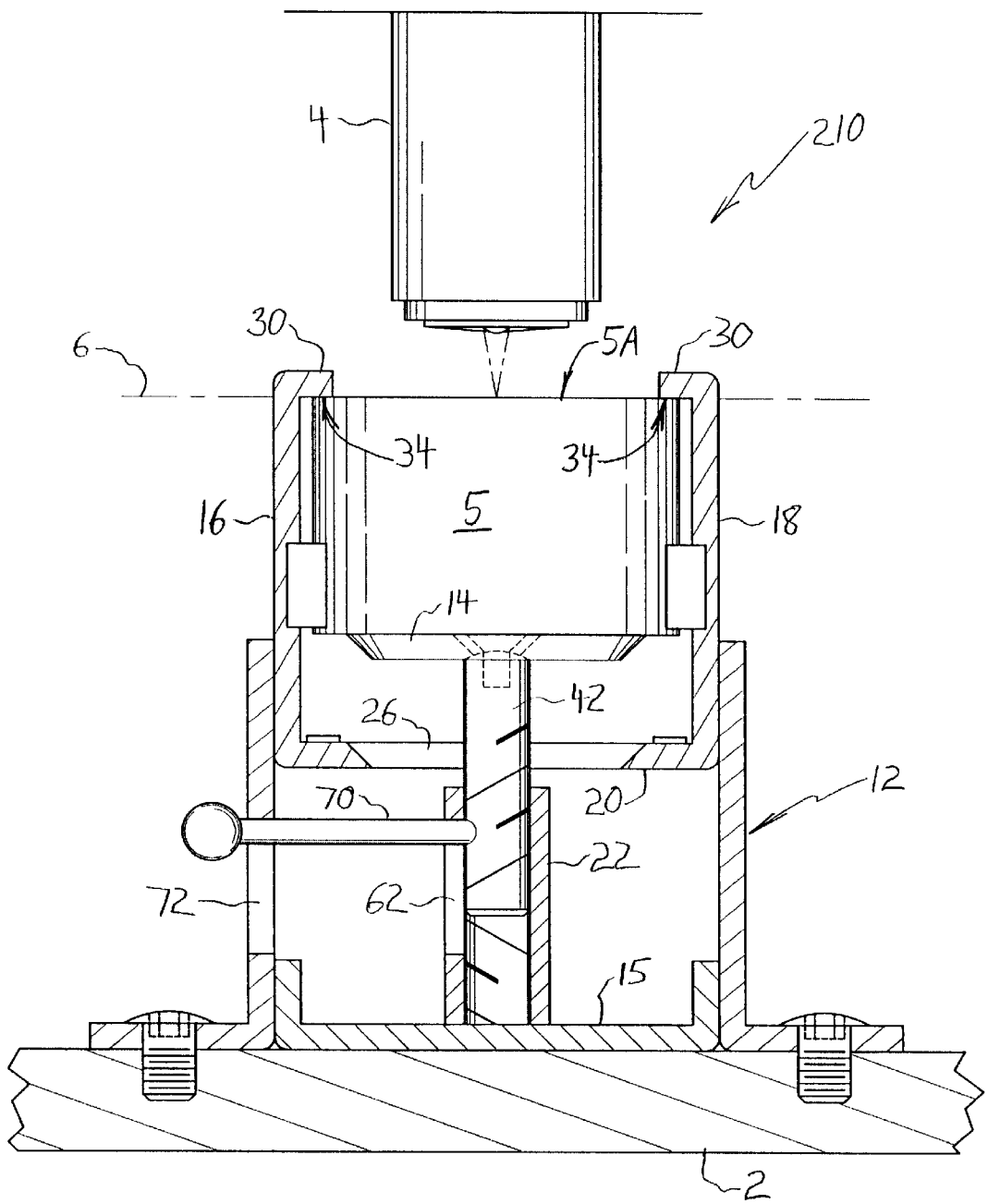
FIG. 5 is a partially sectioned side view of a sample magazine device formed in accordance with a third embodiment of the present invention.
Figure 6:
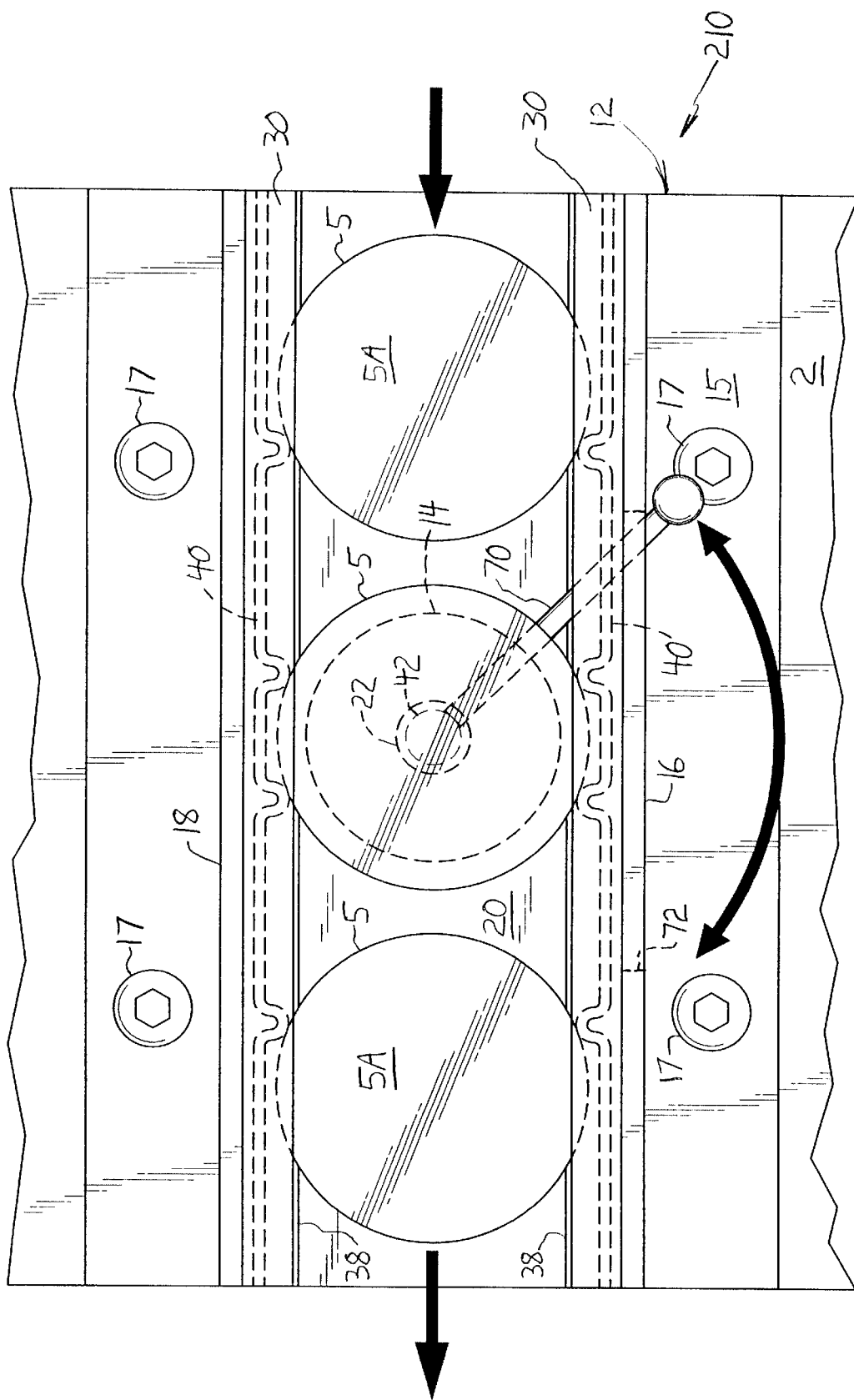
FIG. 6 is a top view of the sample magazine device shown in FIG. 5.

FIGS. 5 and 6 depict a device 210 formed in accordance with a third embodiment of the present invention that differs from the first and second embodiments in that movement stage 14 is manually driven. Device 210 is similar in construction to device 110 of the second embodiment in that it relies on threaded mating between guide sleeve 22 and guided member 42. However, in the third embodiment, a lever 70 extends radially from guided member 42 through opening 62 in guide sleeve 22 and also through an opening 72 in front wall 16. As best seen in FIG. 6 and indicated by the bi-directional arrow, lever 70 can be pivoted manually back and forth to quickly move the stage between its released and test positions.

Those skilled in the art will recognize that many variations are possible with respect to the means for moving stage 14. Possible automatically driven variants include, but are not limited to, motor/drive shaft arrangements and pneumatic piston arrangements. Possible manually driven variants include, but are not limited to, a lever in a vertical keyway having an adjacent catch for holding the lever and stage in the test position against a spring bias.

The present invention allows an operator to quickly test a series of like-sized samples without having to repeatedly adjust the z-stage 2 of the microhardness tester. After the frame 12 has been secured on z-stage 2 by fasteners 17, the z-stage is adjusted such that the engagement surfaces 34 are coplanar with focal plane 6 of objective lens 4. This step can be done with a first sample in place for testing. Once z-stage 2 is properly adjusted, samples are pushed through the frame 12 along on slider strips 38 to align a sample to be tested with stage 14. Then the particular stage movement means is activated, such as by throwing a switch or manually pivoting lever 70, to move the stage 14 upward to its test position wherein test surface 5A is coplanar with focal plane 6. The microhardness tester operates in a known manner to indent the test surface and observe any resulting indentations through objective lens 4. Once the test has been completed, the stage movement means is activated in reverse direction to move stage 14 to its released position. This procedure is then repeated to measure the next sample in line.

What is claimed is:

1. A device for positioning a test surface of a sample in the focal plane of an objective lens of a microhardness tester having a z-stage adjustable in a z-axis direction relative to said objective lens, said device comprising:

a frame having substantially parallel front and rear walls, a bridge wall connecting said front and rear walls, and a base attachable to said z-stage of said microhardness tester;

a pair of inwardly protruding detent rails extending one along said front wall and one along said rear wall, said pair of detent rails each having an engagement surface in said focal plane;

a stage between said front and rear walls for carrying said sample with said sample surface facing said engagement surfaces of said pair of detent rails; and means for moving said stage between a test position wherein said test surface is in surface-to-surface engagement with said engagement surfaces of said pair of detent rails and a released position wherein said test surface is out of surface-to-surface engagement with said engagement surfaces of said pair of detent rails.

2. The device according to claim 1, wherein said front wall and said rear wall each include a spring strip having a plurality of spring stops for releasably aligning said test sample on said stage.

3. The device according to claim 1, wherein said stage is mounted on a swivel coupling.

4. The device according to claim 1, wherein said bridge wall has an opening formed therein, and said stage resides in said opening when said stage is in said released position.

5. The device according to claim 1, wherein said base is releasably attached to said z-stage by a plurality of threaded fasteners.

6. The device according to claim 1, wherein said means for moving said stage comprises an automatic driver.

7. The device according to claim 6, wherein said automatic driver is a solenoid housed under said z-stage, and said stage is connected to a core rod of said solenoid, whereby said stage is moved into said test position by energizing said solenoid and allowed to return to said release position under gravity by de-energizing said solenoid.

8. The device according to claim 7, further comprising a spring between said core rod and said stage for dampening impact of said test surface with said engagement surfaces when said stage is moved to said test position.

9. The device according to claim 6, wherein said means for moving said stage includes a threaded rod connected to said stage and received within a threaded guide sleeve of said frame, and said automatic driver is arranged to effect bi-directional rotation of said threaded rod relative to said threaded guide sleeve to move said stage.

10. The device according to claim 9, wherein said threaded rod includes a lever extending through an opening in said threaded guide sleeve, and said automatic driver acts on said lever to effect rotation of said threaded rod relative to said threaded guide sleeve.

11. The device according to claim 1, wherein said means for moving said stage is manually driven.

12. The device according to claim 11, wherein said means for moving said stage includes a threaded rod connected to said stage and received within a threaded guide sleeve of said frame, a lever coupled to said threaded rod and extending through an opening in said threaded guide sleeve and through an opening in said front wall, whereby a user can manually pivot said lever to effect bi-directional rotation of said threaded rod relative to said threaded guide sleeve to move said stage.

13. The device according to claim 1, wherein said frame is elongated in a lateral direction, whereby at least one additional test sample not aligned on said stage is supported by said bridge wall.

14. The device according to claim 13, wherein said bridge wall includes a pair of low-friction slider strips proximate said front wall and said rear wall, respectively, for slidably supporting said test sample when said stage is in said released position and for slidably supporting said at least one additional test sample, whereby a stream of test samples can be directed laterally through said frame for successive testing.

15. The device according to claim 13, wherein said front wall and said rear wall each include a spring strip having a plurality of spring stops for releasably aligning said test sample on said stage and laterally spacing said at least one additional test sample from said stage.

16. The device according to claim 13, wherein said base is releasably attached to said z-stage by a plurality of threaded fasteners.

17. The device according to claim 13, wherein said means for moving said stage comprises an automatic driver.

18. The device according to claim 17, wherein said automatic driver is a solenoid housed under said z-stage, and said stage is connected to a core rod of said solenoid, whereby said stage is moved into said test position by energizing said solenoid and allowed to return to said release position under gravity by de-energizing said solenoid.

19. The device according to claim 18, further comprising a spring between said core rod and said stage for dampening impact of said test surface with said engagement surfaces when said stage is moved to said test position.

20. The device according to claim 17, wherein said means for Moving said stage includes a threaded rod connected to said stage and received within a threaded guide sleeve of said frame, and said automatic driver is arranged to effect bi-directional rotation of said threaded rod relative to said threaded guide sleeve to move said stage.

21. The device according to claim 20, wherein said threaded rod includes a lever extending through an opening in said threaded guide sleeve, and said automatic driver acts on said lever to effect rotation of said threaded rod relative to said threaded guide sleeve.

22. The device according to claim 13, wherein said means for moving said stage is manually driven.

23. The device according to claim 22, wherein said means for moving said stage includes a threaded rod connected to said stage and received within a threaded guide sleeve of said frame, a lever coupled to said threaded rod and extending through an opening in said threaded guide sleeve and through an opening in said front wall, whereby a user can manually pivot said lever to effect bi-directional rotation of said threaded rod relative to said threaded guide sleeve to move said stage.

* * * * *